(12) United States Patent
Cronauer (10) Patent No.: US 7,963,766 B2
(45) Date of Patent: Jun. 21, 2011

(54) ORTHODONTIC APPLIANCE WITH EMBEDDED WIRE FOR MOVING TEETH

(76) Inventor: Edward A. Cronauer, Weston, FL (US)

( * ) Notice: Subject to any disclaimer, the term of this patent is extended or adjusted under 35 U.S.C. 154(b) by 836 days.

(21) Appl. No.: 11/784,459

(22) Filed: Apr. 6, 2007

(65) Prior Publication Data

US 2007/0184398 A1 Aug. 9, 2007

Related U.S. Application Data

(60) Continuation-in-part of application No. 11/503,591, filed on Aug. 14, 2006, now Pat. No. 7,416,407, which is a division of application No. 10/160,943, filed on May 31, 2002, now Pat. No. 7,104,790.

(51) Int. Cl.
*A61C 7/00* (2006.01)
(52) U.S. Cl. ......................................................... 433/6
(58) Field of Classification Search .................. 433/6, 7, 433/18, 21; 128/861, 862
See application file for complete search history.

(56) References Cited

U.S. PATENT DOCUMENTS

| | | | |
|---|---|---|---|
| 3,334,417 A * | 8/1967 | Spengeman | 433/6 |
| 3,478,742 A | 11/1969 | Bohlmann | |
| 3,724,075 A * | 4/1973 | Kesling | 433/6 |
| 3,837,081 A * | 9/1974 | Kesling | 433/6 |
| 3,994,068 A | 11/1976 | Goshgarian | |
| 4,055,895 A | 11/1977 | Huge | |
| 4,299,568 A | 11/1981 | Crowley | |
| 4,413,978 A | 11/1983 | Kurz | |
| 4,609,349 A | 9/1986 | Cain | |
| 4,793,803 A | 12/1988 | Martz | |
| 4,798,534 A | 1/1989 | Breads | |
| 4,799,884 A | 1/1989 | Bergersen | |
| 5,022,855 A * | 6/1991 | Jeckel | 433/18 |
| 5,203,695 A | 4/1993 | Bergersen | |
| 5,310,340 A | 5/1994 | Zedda | |
| 5,415,542 A * | 5/1995 | Kesling | 433/6 |
| 5,536,169 A | 7/1996 | Yousefain | |
| 5,607,300 A | 3/1997 | Tepper | |
| 5,645,420 A | 7/1997 | Bergersen | |
| 5,836,761 A | 11/1998 | Belvedere et al. | |
| 5,876,199 A | 3/1999 | Bergersen | |
| 5,879,155 A | 3/1999 | Kittelsen | |
| 5,975,893 A | 11/1999 | Chishti et al. | |
| 6,790,036 B2 | 9/2004 | Graham et al. | |
| 7,104,790 B2 * | 9/2006 | Cronauer | 433/6 |
| 7,416,407 B2 * | 8/2008 | Cronauer | 433/6 |

* cited by examiner

*Primary Examiner* — Ralph A Lewis
(74) *Attorney, Agent, or Firm* — Joseph R. Englander; Shutts & Bowen LLP (57) ABSTRACT

The present invention provides an orthodontic appliance including a unitary appliance body positionable about a portion of a single dental arch, where the appliance body may define a lingual portion, a labial-buccal portion, and a contoured portion therebetween. The appliance body may further define an anterior portion and a posterior portion, as well as a first wire coupled to the appliance body, with the first wire extending from the lingual portion of the appliance body to the labial-buccal portion of the appliance body. In addition, a first portion of the first wire may be embedded in the appliance body while a second portion of the first wire extends from the posterior portion of the appliance body. The appliance may further include a second wire disposed about the appliance body between the first wire and the anterior portion of the appliance body. A series of appliances may be used to shift a patient's bite to proper bite orientation.

19 Claims, 5 Drawing Sheets

ORTHODONTIC APPLIANCE WITH EMBEDDED WIRE FOR MOVING TEETH

CROSS-REFERENCE TO RELATED APPLICATION

This application is a continuation-in-part-of patent application Ser. No. 11/503,591, filed Aug. 14, 2006, now U.S. Pat. No. 7,416,407 entitled ORTHODONTIC APPLIANCE WITH EMBEDDED WIRE FOR MOVING TEETH AND METHOD, which application is a divisional application of patent application Ser. No. 10/160,943, filed May 31, 2002, entitled ORTHODONTIC APPLIANCE WITH EMBEDDED WIRE FOR MOVING TEETH AND METHOD, which issued as U.S. Pat. No. 7,104,790, the entirety of each of which is incorporated herein by reference.

STATEMENT REGARDING FEDERALLY SPONSORED RESEARCH OR DEVELOPMENT n/a

FIELD OF THE INVENTION

The present invention relates to an orthodontic method and system for the correction of a patient's bite and alignment of a patient's teeth. Currently, orthodontic appliances apply forces to the teeth of the patient. These forces physically shift the patient's teeth with precise and complex movements, to conform the teeth to a model created by the orthodontist or a laboratory specifically suited to the purpose.

BACKGROUND OF THE INVENTION

Active treatment of the bite historically involved cementing brackets onto the teeth with one or more arch wires attached. While these brackets are unattractive, they have shown that a wire can be used to rapidly move teeth. The present invention relates to the field of orthodontics. In particular, the invention relates to an orthodontic appliance which comprises a wired imbedded in a plastic matrix.

Teeth are generally repositioned by wearing braces, which include brackets, ligatures, O-rings and archwires. Archwires are wires firmly attached to the brackets and are used to exert a force on teeth either on the lingual side or on the labial side. Recently, apparati have been developed which use a flexible thermoplastic that fit entirely over the upper and/or the lower arch. However, these apparati have only a limited ability to move teeth.

An orthodontic appliance is described in U.S. Pat. No. 5,310,340 to Zedda. In Zedda, the appliance has a base and support element in which a steel wire extends from the base and support element to a synthetic resin bracket cemented to a tooth. Another orthodontic appliance is described in U.S. Pat. No. 5,536,169 to Yousefian. In Yousefian, The appliance includes a plurality of arcurate polymer strips which includes a wire extending through the length of the strips with transverse adjusting segments. The appliance requires a lingual strip and a labial strip of polymer.

An orthodontic retainer is described in U.S. Pat. No. 3,994,068 to Goshgarian. In Goshgarian, the retainer includes loops outside the body of the device for accurate adjustment on the labial side of the teeth. U.S. Pat. No. 4,299,568 to Crowley describes an orthodontic retainer in which wires contact tooth surface, and which includes palatial overlays. U.S. Pat. No. 5,203,695 to Bergersen teaches a device with a wire that has a sharp and jutting bend. Moreover, the wire is bent and otherwise adjusted after the appliance is made and fitted for the patient. U.S. Pat. No. 4,413,978 to Kurz describes a retainer with wire hooks anchoring the retainer to molars, and has a wire cemented to the person's arch. U.S. Pat. No. 5,975,893 to Chishti, et al., teaches a clear plastic orthodontic device fitted over all of the patient's teeth which slowly moves the teeth through a system of plastic appliances. However, Chishti only teaches the inefficient and slow use of force on the patient's teeth that is intrinsic to the resiliency in the plastic that forms the appliance.

The prior art inventions either attach brackets directly to the teeth or comprise a plastic device that slowly moves the teeth around the bridge. Also, prior art devices require clasps for the wire to be attached to the device. Prior art inventions also include devices that are costly and difficult to manufacture. Permanently attached braces are unsightly, inconvenient when eating or speaking and may cause discoloration or even pain to the patient. The speed by which the prior art plastic devices move teeth is limited by the rigidity of the plastic used. Not even modern plastics can provide sufficient force to quickly reorient the alignment of the teeth or the bite of a patient.

A need exists in the field of orthodontic devices for an easy to manufacture device which quickly moves teeth into an orthodontically advantageous orientation. A need also exists for a device that is clear and therefore invisible to others and which is relatively pain free when worn. The need also exists for a device which allows the chewing surface of the front teeth or the labial side of the front teeth to be exposed while the appliance is worn. Moreover, the need also exists for a removable orthodontic device with a wire imbedded in the lingual surface, providing the advantage of a flexible, clear device with the benefit of one or more wires to provide invisible force on the teeth. There is also a need for a succession of these devices incorporating wires, allowing intricate movement of the patient's teeth. Additionally, there is a need for a method for making these devices.

The instant invention has been directed to the effective resolution of the aforementioned shortcomings and to the meeting of the aforementioned needs.

SUMMARY OF THE INVENTION

The present invention provides a novel and unique removable appliance that is easy to manufacture and provides an increasingly forceful and less obtrusive movement of teeth while the appliance is worn. The present invention provides relatively pain free and rapid movement of a patient's teeth into a proper orientation. In one embodiment, the invention is a generally horseshoe shaped clear flexible resilient plastic wire-imbedded orthodontic appliance for an upper arch or a lower arch of a patient. The appliance includes a plastic portion with a lingual side, a labial side, a left molar area, a right molar area, a left canine area and a right canine area, and has contours on the lingual side and on the labial side, wherein the contours snugly cover the patient's teeth so that the appliance remains in place over the patient's teeth. One or more flexible wires are imbedded within the lingual or labial side of the plastic portion, extending from the left molar area to the right molar area of the plastic portion, so the wires are able to apply force on the lingual or labial side of the patient's teeth to rapidly correct the orientation of the teeth in the patient's bite.

In an alternative embodiment, the plastic portion covers the surface of the patient's teeth from the left rear molar to the right rear molar. Also, the plastic portion may have a first outer section that covers the entire surface of the patient's teeth from approximately the left molars to the left canines, a second outer section that covers the entire surface of the patient's teeth from approximately the right molars to the right canines, and a middle span that covers only the labial side of the patient's teeth approximately between the canines. In this embodiment, the middle span acts as a guide for the force of the wire upon the patient's teeth.

In still another embodiment, the plastic portion has a first outer section that covers the entire surface of the patient's teeth from approximately the left molars to the left canines, and a second outer section that covers the entire surface of the patient's teeth from approximately the right molars to the right canines. Thus, the plastic portion does not touch the patient's teeth approximately between the patient's canines. Also, a plurality of vertically parallel wires may be imbedded within the lingual or labial side of the plastic portion of the appliance. The appliance may also have vertically parallel wires with a length and cross-sectional shape which optimizes the force applied to the patient's teeth. For example, the cross-sectional shape may be rectangular, round, or oval.

The invention is also a method of forming a generally horseshoe shaped clear flexible resilient plastic wire-imbedded orthodontic appliance for an upper arch or a lower arch of a patient. The method generally includes the steps of obtaining a plaster cast of the patient's teeth and gums, removing plaster teeth from the plaster cast of the gums that are appropriate for the formation of proper tooth alignment, reattaching the appropriate plaster teeth to the plaster cast of the gums to form a cast of the proper tooth alignment, attaching one or more wires to the lingual surface of the plaster teeth so that the wires become imbedded within thermosetting plastic placed over the cast of the proper tooth alignment, putting the cast in a thermosetting plastic molding machine and inserting thermosetting plastic in the thermosetting plastic molding machine, and heating the thermosetting plastic around the cast of the proper tooth alignment so the wires are imbedded within the thermosetting plastic after the thermosetting plastic cools. In one embodiment, the method includes the steps of removing the appliance from the thermosetting plastic molding machine and trimming the lingual surface of the appliance to form a middle span, wherein the span acts as a guide for the pushing force of the wire on the patient's bite.

Moreover, the invention includes a method of rapidly repositioning teeth from an initial alignment to a proper alignment using a generally horseshoe shaped clear flexible resilient plastic wire-imbedded orthodontic appliance for an upper arch or a lower arch of a patient, comprising the steps of placing a first incremental position adjustment appliance over a patient's teeth, wherein the first appliance has at least one wire imbedded within the lingual side of the first appliance to reposition the teeth from the initial tooth alignment to a first intermediate alignment, successively replacing one or more additional appliances, wherein the additional appliances each have at least one wire imbedded within the lingual or labial side to rapidly reposition the teeth from the first intermediate alignment to successive intermediate alignments and placing a final appliance over a patient's teeth, wherein the final appliance has at least one wire imbedded within the lingual side of the first appliance to reposition the teeth, wherein the final appliance positions the teeth from the last intermediate alignment to a final bite alignment. Alternatively, a plurality of vertically parallel wires is imbedded within the lingual side of the first appliance, the intermediate appliances and the final appliance.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
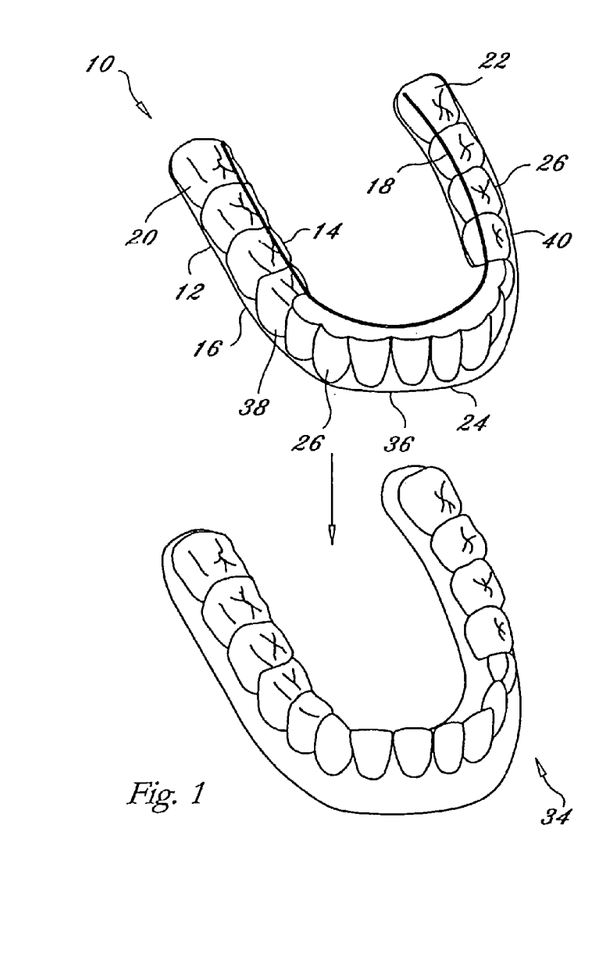
FIG. 1 is a perspective drawing of an embodiment of the invention for an arch of a patient.

Referring now to the drawings and in particular, FIG. 1, the generally horseshoe shaped clear flexible resilient plastic orthodontic appliance for a patient is shown generally at 10. A plastic portion 12 has a lingual side 14 and a labial side 16. Both the lingual side 14 and the labial side 16 have concave contours 26. These contours 26 snugly contact the patient's teeth 34. The contours 26, especially those over the molars, allow the appliance 10 to remain fixed in place over the patient's teeth 34. The contours 26, especially those on the front 36 of the appliance 10, serve the function of guiding the force of the appliance 10 to move the patient's teeth 34 into an advantageous position. On the lingual side 14 of the appliance 10 are one or more flexible wires 18 at least partially embedded within the plastic portion 12.

Preferably, the wires 18 are made of a nickel-titanium alloy or stainless steel, although other similar materials which would provide force on the patient's teeth may also be used. It is also preferred that the diameter of the wire be approximately 12 to 18 thousandths of an inch, or thicker. However, depending upon the force necessary to improve the patient's bite, the wire 18 may be of greater or lesser diameter. The wire 18 may round, oval, square, or some other shape in cross-section which, when used, is advantageous to the patient's bite. Moreover, as shown in FIG. 5, several generally vertically parallel wires 18 may be used.

In the embodiment of FIG. 1, a flexible wire 18 extends generally from a left molar area 20 to a right molar area 22 of the plastic portion 12. However, the wire 18 may alternatively extend from left bicuspid area 38 to right bicuspid area 40 of the plastic portion 12, or extend other areas where the force of the wire 18 would help the patient's bite, such as between two canine teeth of a dental arch. Thus, when worn by the patient, the wires 18 apply force on the lingual or labial side of the patient's bite. The wire 18 thereby aids in the rapid correction of the orientation of the patient's bite while the appliance 10 is in use. The appliance 10 may be used on the patient's upper jaw or the lower jaw, or for use on both jaws simultaneously.

Figure 1A:
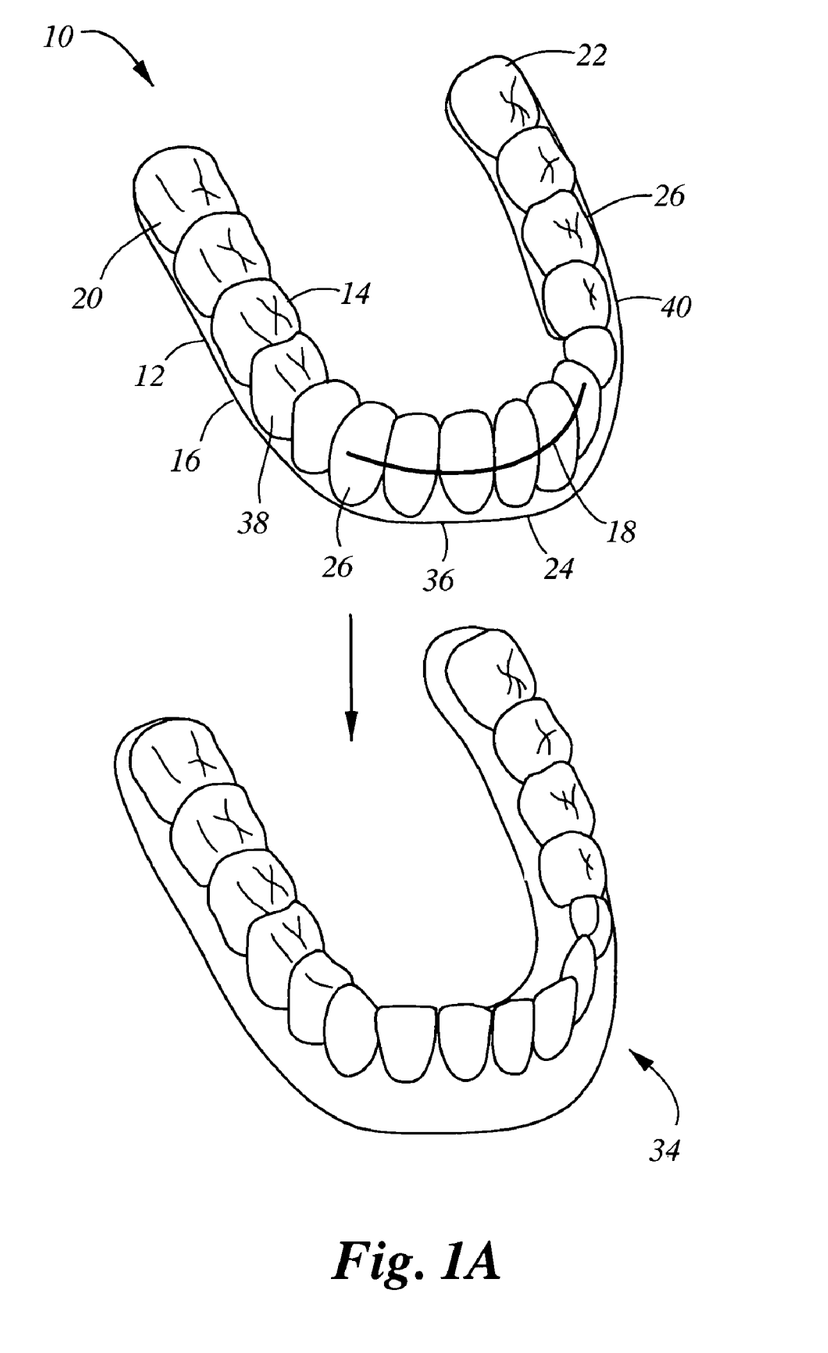
FIG. 1a is a perspective drawing of an alternative embodiment of the invention for an arch of a patient.

In the embodiments shown in FIGS. 1 and 1a, the plastic portion 12 includes a span 24 which covers the patient's teeth from the left canine area 30 to a right canine area 32. This span 24 also contains contours 26 as described above. As illustrated in FIG. 1, the plastic portion 12 preferably covers the entire front surface of the patient's teeth from the patient's molars approximately to the patient's canines, and the span 24 covers the labial side of the teeth approximately between the canines. Thus the span 24 across the labial side of the patient's teeth acts as a guide for the force of the wire 18. As shown in FIG. 5, multiple parallel wires 18 may be used on the labial and/or lingual side of the appliance 10, thereby increasing the moving force on the patient's teeth. To precisely apply force on the teeth, wires of varying strength, diameter and cross sectional shape may be used. For example, although wires 18 with rectangular cross-section are shown in FIG. 4, round or oval wires 18 may be used.

Figure 2:
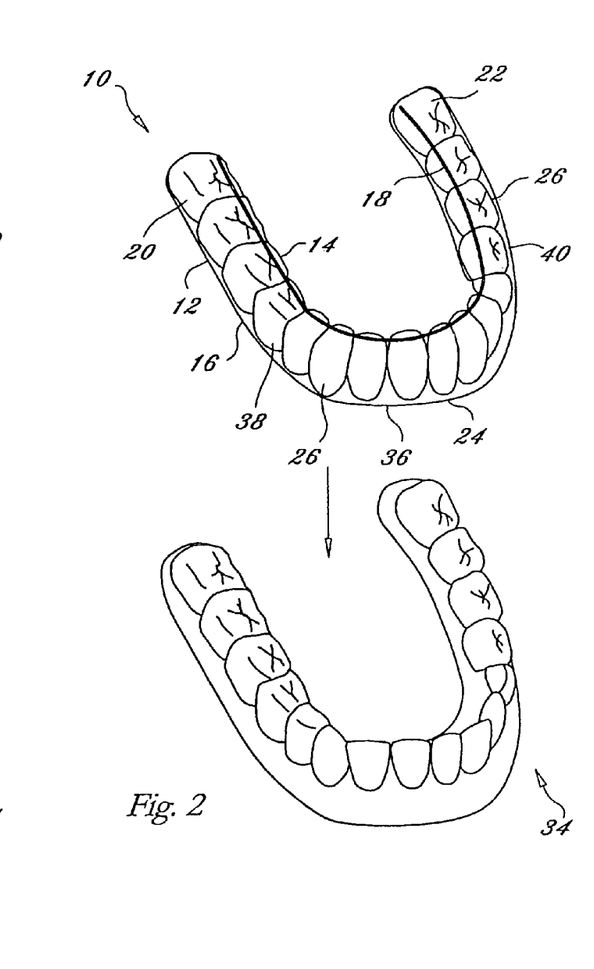
FIG. 2 is a perspective drawing of an alternative embodiment of the invention for an arch of a patient.
Figures 2A, 3, 4, 5:
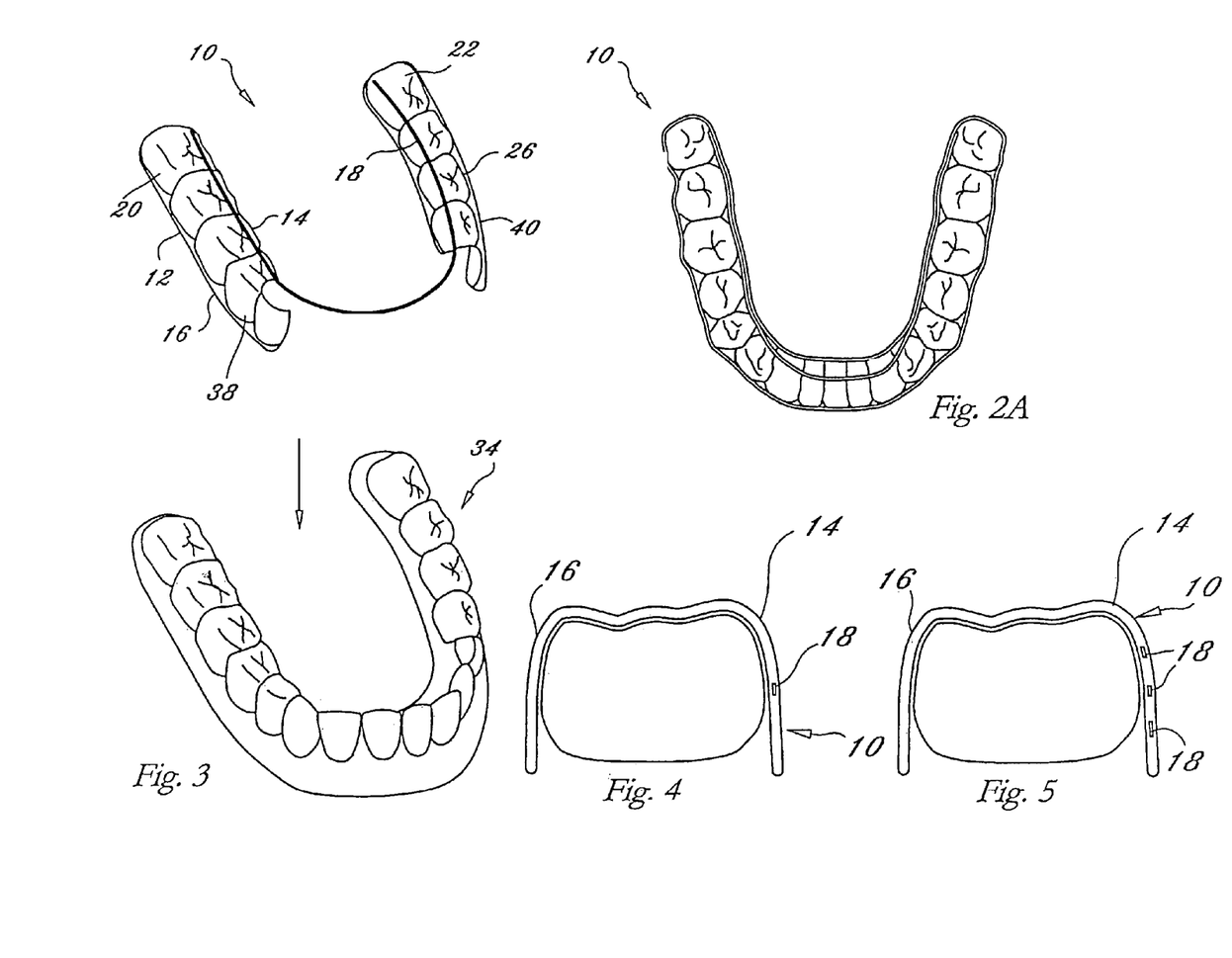
FIG. 2a is a top view of an alternative embodiment of the invention for an arch of a patient.
FIG. 3 is a perspective drawing of an embodiment of the invention for an arch of a patient.
FIG. 4 is a cross sectional view of an embodiment of the invention for an arch before it is placed on a patient.
FIG. 5 is a cross sectional view of an alternative embodiment of the device with several generally parallel wires embedded within the lingual surface of the appliance.

An alternative embodiment is shown in FIGS. 2 and 2a. In this embodiment, the appliance 10 comprise contours which cover the patient's teeth entirely. An additional alternative embodiment is shown in FIG. 3. In FIG. 3, the appliance 10 covers the patient's teeth only from approximately the left molar to approximately the left canine and from approximately the right molar to approximately the right canine. As shown in FIG. 3, one wire 18 or a plurality of vertically parallel wires 18 are imbedded within the lingual side of the appliance 10. Although not shown in FIGS. 2-3, it is understood that the one or more wires may also be disposed on the labial side, as described above and as illustrated in FIG. 1a. Such an appliance may be in situations where the guidance of the plastic contours of the span 24 is not necessary, or where it is advantageous for the patient to have no covering over the front teeth while the appliance 10 is worn. Moreover, the one or more wires 18 may be attached to the plastic portion only at each end of the one or more wires 18. In this embodiment, the plastic portion has a void on the labial side and still has contours on the lingual side of the appliance. Alternatively, the plastic portion may only extend from the ends of the wire. In that embodiment, the plastic portion extends only from each end of the wire on the labial side.

Figure 6:
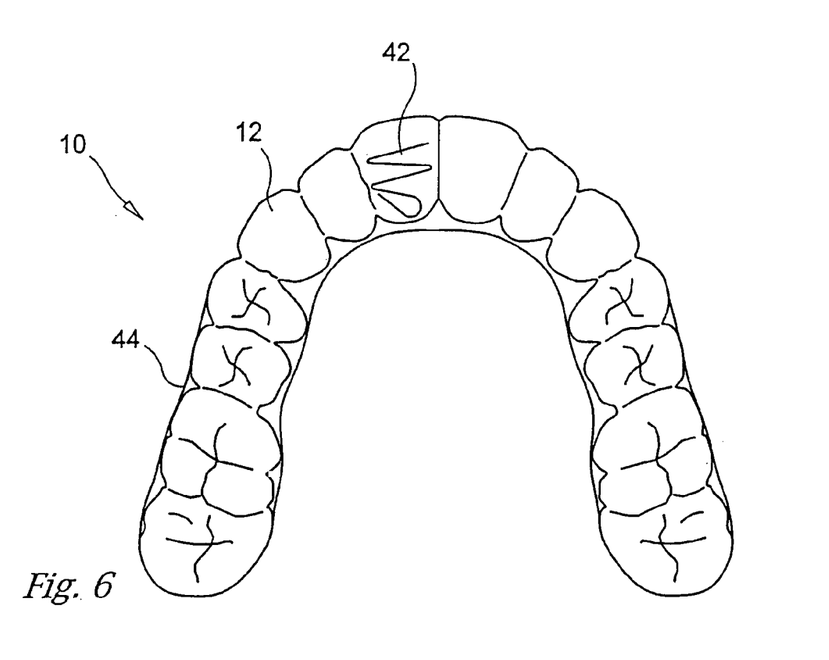
FIG. 6 is a top view of an embodiment of the invention for an arch of a patient.
Figure 7:
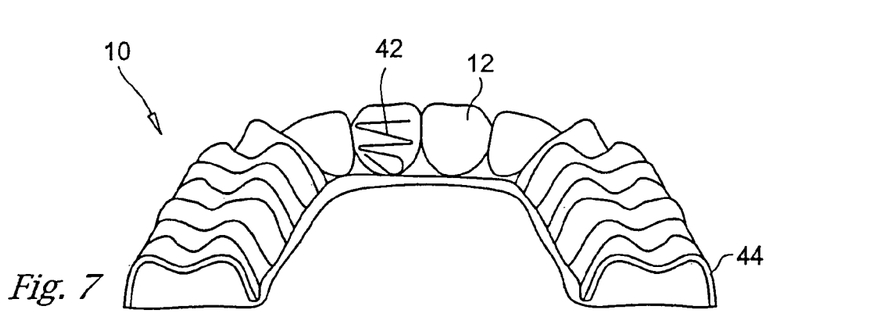
FIG. 7 is a back perspective view of an embodiment of the invention for an arch of a patient.
Figure 8:
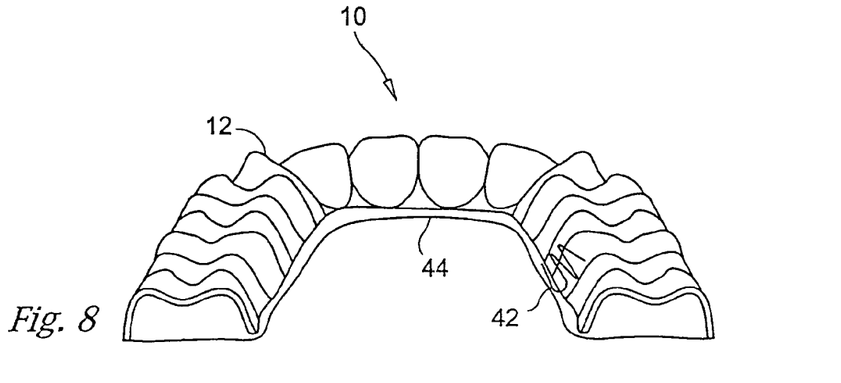
FIG. 8 is a back perspective view of an embodiment of the invention for an arch of a patient.

In another alternative embodiment, shown in FIGS. 6-8, the plastic portion 12 of the appliance 10 covers the entire surface of the patient's teeth from left molar to right molar, FIGS. 6-8 show this embodiment for a patient's lower arch. One or more small fingers springs 42 are pre-fabricated and incorporated into the plastic portion during molding. The finger spring 42 may be located in the lingual side of the plastic portion 12, on the front teeth as shown in FIGS. 6-7 or on a molar as shown in FIG. 8. Alternatively, the finger spring may be located in the buccal side of the plastic portion. In addition, during the formation of the appliance 10, on the plaster model of the patient's arch used to make the appliance 10, the opposite side of the tooth 44 affected by the finger spring 42 may be built up with modeling clay to make a void in the appliance 10. The patient's tooth is then able to move into the void as pressure is applied to the tooth on the labial side by the finger spring 42. The use of the void allows selective movement of an individual tooth. However, several finger springs 42 may be used in this manner on a particular appliance 10. Finger springs 42 are preferably made of 0.014, 0.018 or thicker wire, and are preferably made of stainless steel, nickel titanium alloy or an equivalent material.

The plastic structure 12 in this embodiment may also be the open structure as shown in FIGS. 1 and 3. Typical finger springs are made by Great Lakes Lab, Inc. or Pro Positioner, Inc.; however, they may also be made by hand. More or less pressure may be applied to a tooth by deforming the spring with pliers. Furthermore, the use of progressive springs on a tooth may be used on progressive appliances as described below.

A method of forming the appliance 10 of this invention is as follows. A plaster cast of the patient's teeth and gums is taken by means already well known in the field of orthodontics. Then, appropriate plaster teeth are removed from the plaster cast of the gums, and reattached with modeling clay, floral arrangement putty or equivalent means to the plaster cast of the gums in a proper bite alignment. One or more wires or one or more finger springs are attached to either the lingual or labial surface of the plaster teeth using a means for attachment such as modeling clay or sculpting clay. The means for attachment must allow the wires to become imbedded within thermosetting plastic to be placed over the cast as described below. The cast of the properly aligned teeth is then put in a thermosetting plastic molding machine, preferably the Raintree Essix Amplified Vacuum Thermoforming Machine, or an equivalent compression vacuum machine. Also, a compression machine that operates on heated thermoplastic could also make the appliance, such as the compression machine made by Biostar, Inc. The appliance is then made by inserting thermosetting plastic in the compression vacuum machine or the compression machine. The thermosetting plastic is heated and flows around the cast of the aligned teeth and gums. Preferably, Essix C+ thermoplastic is used, although other plastics with equivalent physical properties are known in the art. The wires 18 are thus imbedded within the appliance 10 formed by the thermosetting plastic when the plastic cools. Preferably, the appliance 10 is removed from the machine and the lingual side of the appliance is trimmed to the general appearance of FIG. 1. However, the appliance may be untrimmed to provide the appliance as generally shown in FIG. 2 or trimmed to remove all thermoplastic from the front teeth, as shown in FIG. 3. Thus, when worn, the wire 18 will act as the manipulating force on the patient's teeth, while in the embodiments shown in FIGS. 1 and 2 the span 24 of the plastic portion 12 acts as a guide for the future placement of the patient's foremost teeth.

A series of appliances 10 with intermediate positions of the bite of the patient may be also formed. A series of appliances 10 may be employed where complex movements are necessary to properly align the teeth of a patient. As above, the plaster teeth are removed from the plaster cast, and reattached to the plaster cast of the patient's gums with a material such as modeling clay, floral arrangement putty or the equivalent. However, the plaster teeth are serially reattached in one or more intermediate positions, and a plastic appliance is created from each of the intermediate positions.

Thus, when the appliances 10 are formed, the patient wears the appliances in series, and the patient's bite is progressively corrected until the final appliance 10 is used. The final appliance 10 properly aligns the patient's bite into proper alignment. Moreover, the wire or wires 18 in the intermediate appliances 10 may be varied as to number, thickness, shape and material to best and most quickly and efficiently alter the patient's bite at each intermediate step. This series would move faster than any series of appliances known in the prior art, because the imbedded wire would move the patient's teeth more rapidly than any plastic appliance in the prior art.

A method for rapidly repositioning teeth from an initial arrangement to a final arrangement using a series of appliances as disclosed comprises of the following steps. A first incremental position adjustment appliance is placed over a patient's teeth, wherein the first appliance is plastic and has at least one wire imbedded within the lingual or labial side of said first appliance to reposition the teeth from the initial tooth arrangement to a first intermediate arrangement. Then, one or more additional appliances are successively replaced on the patient, wherein the additional appliances each have at least one wire imbedded within the lingual or labial side to rapidly reposition the teeth from the first intermediate arrangement to successive intermediate arrangements. Eventually, a final appliance is placed over a patient's teeth. Like the prior appliances, the final appliance has at least one wire imbedded within either the lingual or labial side of the first appliance to reposition the teeth, and the final appliance positions the teeth from the last intermediate arrangement to a final tooth arrangement.

In one alternative embodiment, a plurality of vertically parallel wires is imbedded within the lingual or labial side of the first appliance, the additional appliances and the final appliance. In other embodiments, the shapes of the wires utilized are of different shapes to better apply forces on the patient's teeth.

Figure 9:
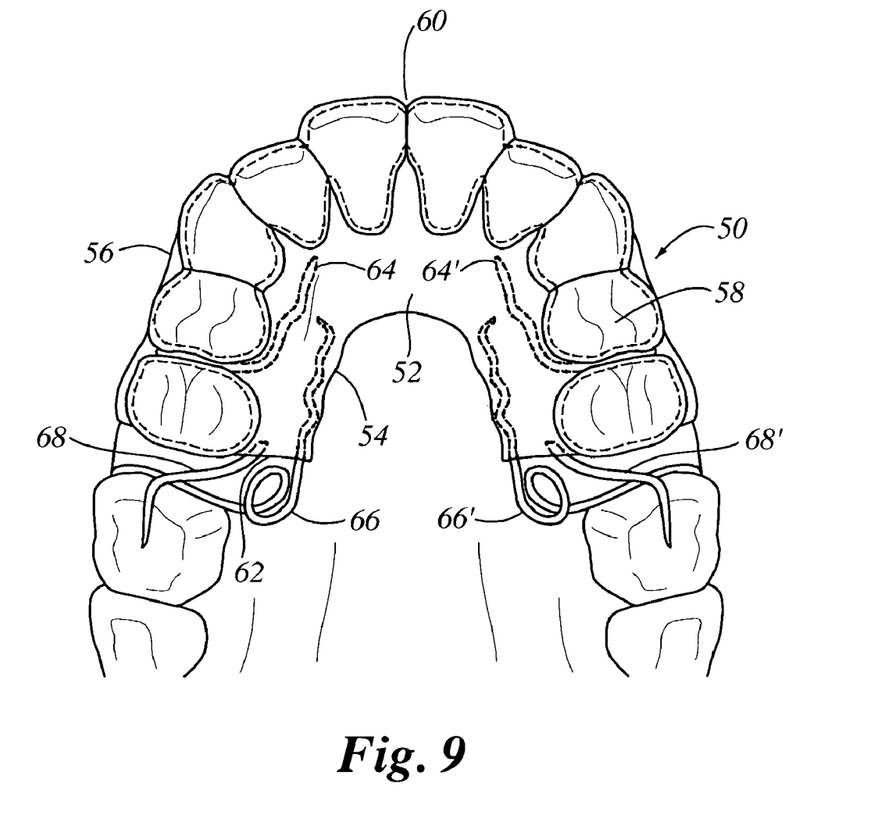
FIG. 9 illustrates an embodiment of an orthodontic appliance in accordance with the present invention.
Figure 10:
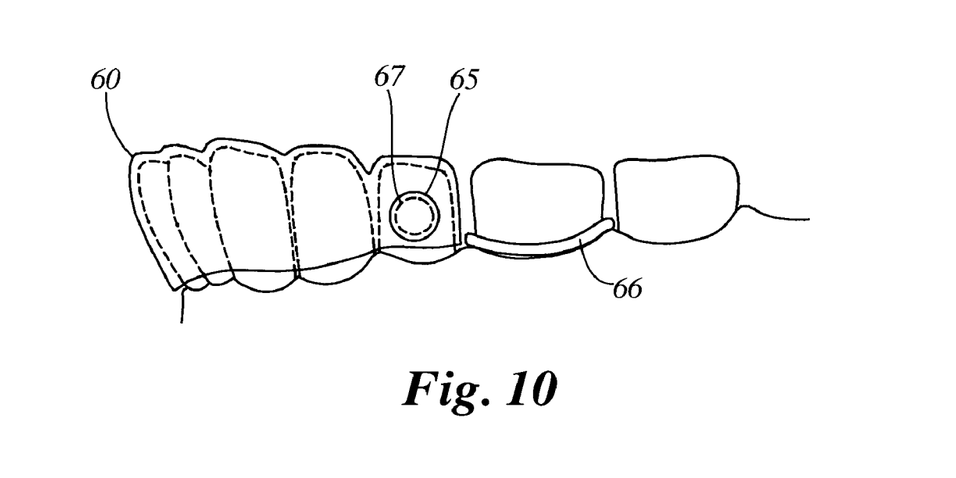
FIG. 10 is a side view of an embodiment of an orthodontic appliance in accordance with the present invention.

Now referring to FIGS. 9 and 10, in an additional embodiment of the present invention, an orthodontic appliance 50 is provided having one or more wires or similar dental shaping elements for providing movement of one or more teeth. In particular, the orthodontic appliance 50 may define an appliance body 52 having a lingual portion 54 facing towards an interior portion of the mouth, a labial/buccal portion 56 facing or otherwise positioned outward towards the lips or cheek, and a contoured portion 58 located therebetween for positioning the orthodontic appliance 50 about one or more teeth of a patient. The orthodontic appliance 50 may further define an anterior portion 60 and a posterior portion 62, where the anterior portion 60 is positionable about one or more teeth towards the front or anterior segment of a patient's mouth (such as the canines and/or incisors), while the posterior portion 62 may be positionable about one more teeth in the rear or posterior segment of a patient's mouth (such as the molars and/or bicuspids). The appliance body 52 may further define a substantially horseshoe-like shape to conform to at least a portion of either the upper or lower arch of teeth of the patient. In addition, the appliance body 52 may have a unitary construction fabricated from a flexible, resilient plastic or similar polymer to allow for some deformational or elastic capacity upon implantation.

As discussed above, the orthodontic appliance 50 may include one or more dental shaping elements, such as wires, spring or the like, embedded in or otherwise coupled to at least a portion of the appliance body 52. For example, one or more anterior wires 64, 64' may be embedded in the appliance body 52 towards the anterior portion 60 of the device. Each anterior wire 64 may include a portion positionable within a space or junction between two teeth, such as an incisor and a canine, a canine and a bicuspid, or between two bicuspids for example, in order to provide for the retention of the appliance and/or repositioning or relative manipulation of the desired teeth over a period of time.

Furthermore, the one or more anterior wires 64, 64' may extend from the lingual portion 54 of the orthodontic appliance 50, between the two subject teeth towards the labial portion 56 of the orthodontic appliance 50, thus forming somewhat of a U-shape when viewed from a horizontal plane of reference. The one or more anterior wires 64, 64' may include various bends or contours to provide a resilient force between two or more teeth, as well as to provide for anchoring and/or improved positioning about a desired segment of a dental arch. Moreover, the one or more anterior wires 64, 64' may be completely or substantially embedded within the appliance body 52. The anterior wires may also be exposed on a buccal side or a side of the orthodontic appliance 50 exposed to the gums.

In addition and/or alternatively to the anterior wires, the appliance body 52 may define a protruding portion 65, such as a rounded "bump" or the like that may aid in anchoring and holding the orthodontic appliance in a desired position. This protruding portion may be hollow. The protruding portion 65 may couple to a button or similar anchoring element 67 that is affixed to a surface of a tooth prior to placement of the orthodontic appliance. The surface may be a side surface of the tooth. For example, upon initially shaping or forming the orthodontic appliance, whether through the use of imaging or taking an impression, etc., an acrylic button or other suitable anchoring element may be affixed to either the tooth of a patient and/or a mold taken from the patient. Subsequently, the orthodontic appliance may be formed using the resulting cast of the teeth or imaging having the anchoring element positioned on the tooth or by similar method. As a result, the shape and contours of the orthodontic appliance will include the corresponding protruding portion, which results from, and is therefore engageable with, the anchoring element. In essence, the orthodontic appliance will be able to "snap" into place or otherwise couple to the anchoring element to reduce movement relative to the tooth or loosening of the appliance when in use.

The orthodontic appliance 50 may also include one or more posterior wires 66, 66' coupled to the posterior portion 62 of the appliance body 52. For example, one or more posterior wires 66, 66' may extend from the posterior portion 62 of the appliance body 52 and towards a more posterior segment of the arch about which the orthodontic appliance 50 may be positioned in order to manipulate and/or otherwise change the relative location of two or more teeth. A posterior wire may have a least a portion or segment of its length embedded in or otherwise coupled to the appliance body 52, while another portion of the posterior wire may then extend outward to be positionable between the appliance body 52 and one or more teeth located posterior to the appliance body 52. Similar to that of the anterior wires described above, the posterior wire may include a contoured or bended configuration to provide a resilient and/or resistive force when the orthodontic appliance 50 is positioned about a dental arch. In a particular example, the one or more posterior wires may include a coil or wound portion of wire.

The orthodontic appliance 50 may also include one or more wires proximate the posterior portion of the appliance body to intrude or otherwise apply a force on a desired tooth in a superior/inferior direction (i.e., cranial/caudal). In particular, the orthodontic appliance may include one or more intruding wires 68, 68' extending from the appliance body and extending to contact a biting surface of a tooth. Similar to the wires described above, the intruding wires 68, 68' may include a contoured or bended configuration to provide a resilient and/or resistive force when the orthodontic appliance 50 is positioned about a dental arch. The one or more intruding wires 68, 68' may apply a force to the biting surface of a desired tooth, thereby causing the intrusive movement of the particular tooth being affected. In addition, as the thickness of the appliance body 52 creates some clearance between the upper and lower arches when biting down, the one or more intruding wires 68, 68' are not affected by and thus do not otherwise interfere with a patient's bite. As a result, the likelihood that the intruding wires will be damaged or modified during the course of use is reduced should the patient bite down.

The orthodontic appliance 50 may be constructed through similar methods as described above, and may include taking an impression or image of a patient's teeth and gums. The impression or image may subsequently be used to construct a model of the teeth and the subsequent shaping or manipulation thereof to provide the desired alignment and/or bite mechanics. Ultimately, the appliance body 52 may be suitably shaped for positioning about a dental arch of a patient, and one or more anterior and/or posterior wires may be included with the appliance body 52 to provide for the desired resilient or resistive forces upon the teeth. Furthermore, wires of varying shape, strength, diameter, or the like may be employed to provide for a particular degree of force on a portion of a dental arch.

In an exemplary use of the orthodontic appliance 50, the appliance is constructed from a mold or impression of the patient's teeth as described, which may include selecting one or more particular anterior, posterior, and/or intruding wires and embedding or otherwise coupling the wires to the appliance body 52. The orthodontic appliance 50 may then be positioned about a dental arch of a patient, with the one or more anterior wires 64, 64' providing an anchoring between two or more teeth, and may further provide for a separating force between two or more teeth. Moreover, the posterior wires 66, 66' may be positioned between two or more teeth, where the posterior wires extend from the appliance body 52 to provide a resistive force between the two or more teeth. In particular, the posterior wires may provide a manipulative force to expand the spacing between two molars and/or bicuspids in the rear portion of the dental arch. As the posterior wires may be contoured or otherwise formed to provide varying degrees of resistive force, by anchoring or positioning the appliance body 52 around a portion of the dental arch, the posterior wires may thus push against one or more teeth to create a space therebetween, which may include moving one or more molars distally or otherwise towards the posterior portion of the mouth. In addition, where the orthodontic appliance includes one or more intruding wires 68, 68', placement of the appliance over a portion of the dental arch will cause the intruding wires to impart an intrusive force across a biting surface of a desired tooth. Of course, the intruding wire may be configured through either a particular contoured configuration or by a particular material selection to impart the desired degree of force. Of note, multiple orthodontic appliances may be subsequently constructed to provide for the gradual repositioning of a portion of the dental arch when a particular device no longer provides the desired amount of resistance or force to the teeth as they are effectively moved over time.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An orthodontic appliance for a single dental arch of a patient, comprising:
   a unitary appliance body for the single dental arch defining
      a lingual portion,
      a labial-buccal portion, and
      a contoured portion therebetween positionable about a portion of a dental arch,
   wherein the appliance body further defines an arch shape having two ends forming a posterior portion and anterior portion therebetween; and
   a first wire coupled to the appliance body,
   wherein the first wire is at least partially embedded in the posterior portion of the appliance body, and
   wherein the first wire is positionable to apply a force between the posterior portion of the appliance body and at least one tooth located behind the posterior portion of the appliance body, and
   wherein the unitary appliance body is completely removable from the single dental arch.

2. The orthodontic appliance according to claim 1, wherein the first wire extends from the lingual portion of the appliance body to the labial-buccal portion of the appliance body.

3. The orthodontic appliance according to claim 1, further comprising a second wire disposed about the appliance body between the first wire and the anterior portion of the appliance body.

4. The orthodontic appliance according to claim 3, wherein the second wire extends from the lingual portion of the appliance body to the labial-buccal portion of the appliance body.

5. The orthodontic appliance according to claim 1, further comprising an intruding wire coupled to the posterior portion of the appliance body, wherein the intruding wire is positionable across a biting surface of a tooth of the dental arch.

6. The orthodontic appliance according to claim 1, wherein the unitary appliance body is positionable about a portion of a single dental arch.

7. The orthodontic appliance according to claim 1, wherein the unitary appliance body is constructed from a resilient plastic.

8. The orthodontic appliance according to claim 1, wherein the unitary appliance body is substantially transparent.

9. The orthodontic appliance according to claim 1, wherein at least a portion of the first wire includes a coil.

10. An orthodontic appliance for a dental arch of a patient, comprising:
    a unitary appliance body for a single dental arch defining a lingual portion, a labial-buccal portion, and a contoured portion therebetween positionable about a portion of a dental arch,
    wherein the appliance body further defines an arch shape having two ends forming a posterior portion and anterior portion therebetween;
    a first wire coupled to the appliance body,
    wherein the first wire is at least partially embedded in the posterior portion of the appliance body, and
    wherein the first wire is positionable to apply a force between the posterior portion of the appliance body and at least one tooth located behind the posterior portion of the appliance body, the first wire extending from the lingual portion of the appliance body to the labial-buccal portion of the appliance body; and
    a second wire disposed about the appliance body between the first wire and the anterior portion of the appliance body, and wherein the unitary appliance body is completely removable from the single dental arch.

11. The orthodontic appliance according to claim 10, wherein the second wire extends from the lingual portion of the appliance body to the labial-buccal portion of the appliance body.

12. The orthodontic appliance according to claim 10, further comprising an intruding wire coupled to the posterior portion of the appliance body, wherein the intruding wire is positionable across a biting surface of a tooth of the dental arch.

13. The orthodontic appliance according to claim 10, wherein the unitary appliance body is positionable about a portion of a single dental arch.

14. The orthodontic appliance according to claim 10, wherein the unitary appliance body is constructed from a resilient plastic.

15. The orthodontic appliance according to claim 10, wherein the unitary appliance body is substantially transparent.

16. The orthodontic appliance according to claim 10, wherein at least a portion of the first wire includes a coil.

17. An orthodontic appliance for a single dental arch of a patient, comprising:
- a unitary appliance body positionable about a portion of a single dental arch, the appliance body defining a lingual portion, a labial-buccal portion, and a contoured portion therebetween positionable about a portion of a dental arch,
- wherein the appliance body further defines arch shape having two ends forming a posterior portion and an anterior portion therebetween; and
- an intruding wire coupled to the posterior portion of the appliance body,
- wherein the intruding wire is positioned across a biting surface of a tooth that is located behind the posterior portion of the appliance body when the appliance body is positioned on the dental arch, and
- wherein the unitary appliance body is completely removable from the single dental arch.

18. The orthodontic appliance according to claim 17, further comprising a second wire disposed about the appliance body between the intruding wire and the anterior portion of the appliance body.

19. An orthodontic appliance for a single dental arch of a patient, comprising:
- a unitary appliance body defining
- a lingual portion,
- a labial-buccal portion, and
- a contoured portion therebetween positionable about a portion of the single dental arch,
- wherein the appliance body further defines and arch shape having two ends forming a posterior portion and anterior portion therebetween;
- a first wire coupled to the appliance body,
- wherein the first wire is at least partially embedded in the posterior portion of the appliance body, and
- wherein the first wire is positionable to apply a force between the posterior portion of the appliance body and at least one tooth located behind the posterior portion of the appliance body, the first wire extends from the lingual portion of the appliance body to the labial-buccal portion of the appliance body; and
- a second wire disposed about the appliance body between the first wire and the anterior portion of the appliance body and wherein the unitary appliance body is completely removable from the single dental arch.

* * * * *